(12) United States Patent
Miller et al.

(10) Patent No.: US 7,709,438 B2
(45) Date of Patent: May 4, 2010

(54) AZEOTROPE COMPOSITIONS COMPRISING NONAFLUOROPENTENE AND HYDROGEN FLUORIDE AND USES THEREOF

(75) Inventors: Ralph Newton Miller, Newark, DE (US); Mario Joseph Nappa, Newark, DE (US); Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 759 days.

(21) Appl. No.: 11/590,457

(22) Filed: Oct. 31, 2006

(65) Prior Publication Data

US 2007/0099811 A1 May 3, 2007

Related U.S. Application Data

(60) Provisional application No. 60/732,320, filed on Nov. 1, 2005.

(51) Int. Cl.
*C11D 7/50* (2006.01)
(52) U.S. Cl. .............. 510/408; 510/407; 510/411; 510/412
(58) Field of Classification Search .......... 510/407, 510/408, 411, 412
See application file for complete search history.

(56) References Cited

U.S. PATENT DOCUMENTS

| | | | |
|---|---|---|---|
| 4,978,649 A | 12/1990 | Surovikin et al. | |
| 5,171,902 A | 12/1992 | Krespan et al. | |
| 5,268,122 A | 12/1993 | Rao et al. | |
| 6,191,328 B1* | 2/2001 | Kitano et al. | 570/180 |
| 6,194,619 B1 | 2/2001 | Rao et al. | |
| 6,294,055 B2* | 9/2001 | Herkelmann et al. | 203/43 |
| 6,521,803 B1* | 2/2003 | Lambert et al. | 570/177 |
| 7,063,823 B2* | 6/2006 | Koizumi | 423/3 |
| 7,074,434 B2* | 7/2006 | Lambert et al. | 424/673 |
| 2001/0004961 A1* | 6/2001 | Herkelmann et al. | 203/43 |
| 2005/0080303 A1* | 4/2005 | Sekiya et al. | 570/176 |
| 2007/0099811 A1* | 5/2007 | Miller et al. | 510/408 |

FOREIGN PATENT DOCUMENTS

WO   WO 93/05002   3/1993

OTHER PUBLICATIONS

Schotte, "Collection of Phase Equilibrium Data for Separation Technology", Ind. Eng. Chem. Process Des. Dev. 19 (1980), pp. 432-439.
Null, "Phase Equilibrium in Process Design", Wiley-Interscience Publisher (1970), pp. 124-126.
Walas, "Phase Equilibria in Chemical Engineering—Activity Coefficients", Butterworth Publishers (1985), pp. 165-244.

* cited by examiner

*Primary Examiner*—Gregory E Webb

(57) ABSTRACT

Disclosed herein are azeotrope compositions comprising 1,2,3,3,3-pentafluoropropene and hydrogen fluoride. The azeotrope compositions are useful in processes to produce and in processes to purify 1,2,3,3,3-pentafluoropropene. Additionally, disclosed herein are azeotrope and near-azeotrope compositions comprising 1,1,1,2,3,4,4,5,5,5-decafluoropentane and hydrogen fluoride.

9 Claims, 1 Drawing Sheet

AZEOTROPE COMPOSITIONS COMPRISING NONAFLUOROPENTENE AND HYDROGEN FLUORIDE AND USES THEREOF

BACKGROUND OF THE INVENTION

1. Field of the Invention

Disclosed herein are azeotrope compositions comprising nonafluoropentene and hydrogen fluoride. The azeotrope compositions are useful in processes to produce and in processes to purify nonafluoropentene.

2. Description of Related Art

Chlorine-containing compounds, such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, containing one or more hydrogens in the molecule, are being considered for use in some of the applications, like for example in refrigeration.

BRIEF SUMMARY OF THE INVENTION

One aspect relates to an azeotrope or near-azeotrope composition comprising 1,1,1,3,4,4,5,5,5-nonafluoro-2-pentene (Z-HFC-1429mzy, $CF_3CH=CFCF_2CF_3$) and 1,1,1,2,4,4,5,5-nonafluoro-2-pentene (Z-HFC-1429myz, $CF_3CF=CHCF_2CF_3$) and hydrogen fluoride (HF).

A further aspect relates to a process for the separation of Z-HFC-1429 from 1,1,1,2,3,4,4,5,5-decafluoropentane (HFC-43-10mee) comprising: a) forming a mixture of Z-HFC-1429, HFC-43-10mee, and hydrogen fluoride; and b) subjecting said mixture to a distillation step from which is formed a column distillate composition comprising an azeotrope or near-azeotrope composition of hydrogen fluoride and Z-HFC-1429 essentially free of HFC-43-10mee.

A further aspect relates to a process for the separation of Z-HFC-1429 from a mixture comprising an azeotrope or near-azeotrope composition of Z-HFC-1429 and hydrogen fluoride, said process comprising: a) subjecting said mixture to a first distillation step in which a composition enriched in either (i) hydrogen fluoride or (ii) Z-HFC-1429 is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

A further aspect relates to a process for the purification of Z-HFC-1429 from a mixture of Z-HFC-1429, HFC-43-10mee, and hydrogen fluoride, said process comprising: a) subjecting said mixture to a first distillation step to form a first distillate composition comprising an azeotrope or near-azeotrope composition containing Z-HFC-1429 and hydrogen fluoride and a first bottoms composition comprising HFC-43-10mee; b) subjecting said first distillate composition to a second distillation step from which a composition enriched in either (i) hydrogen fluoride or (ii) Z-HFC-1429 is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with the third bottoms composition enriched in the same component that was enriched in the second distillate composition.

A further aspect relates to a process to produce Z-HFC-1429 comprising: a) feeding HFC-43-10mee to a reaction zone for dehydrofluorination to form a reaction product composition comprising Z-HFC-1429, unreacted HFC-43-10mee and hydrogen fluoride; b) subjecting said reaction product composition to a first distillation step to form a first distillate composition comprising an azeotrope or near-azeotrope composition containing Z-HFC-1429 and hydrogen fluoride and a first bottoms composition comprising HFC-43-10mee; c) subjecting said first distillate composition to a second distillation step from which a composition enriched in either (i) hydrogen fluoride or (ii) Z-HFC-1429 is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed in a third distillate composition with the third bottoms composition enriched in the same component that was enriched in the second distillate composition.

A further aspect relates to a process for the separation of HFC-43-10mee from a mixture comprising an azeotrope or near-azeotrope composition of HFC-43-10mee and hydrogen fluoride, said process comprising: a) subjecting said mixture to a first distillation step in which a composition enriched in either (i) hydrogen fluoride or (ii) HFC-43-10mee is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed as a second distillate composition with the bottoms composition of the second distillation step enriched in the same component which was enriched in the first distillate composition.

A further aspect relates to an azeotrope or near-azeotrope composition comprising 1,1,1,2,3,4,4,5,5,5-decafluoropentane (HFC-43-10mee) and hydrogen fluoride (HF).

BRIEF DESCRIPTION OF THE DRAWING(S)

DETAILED DESCRIPTION OF THE INVENTION

Figure 2:
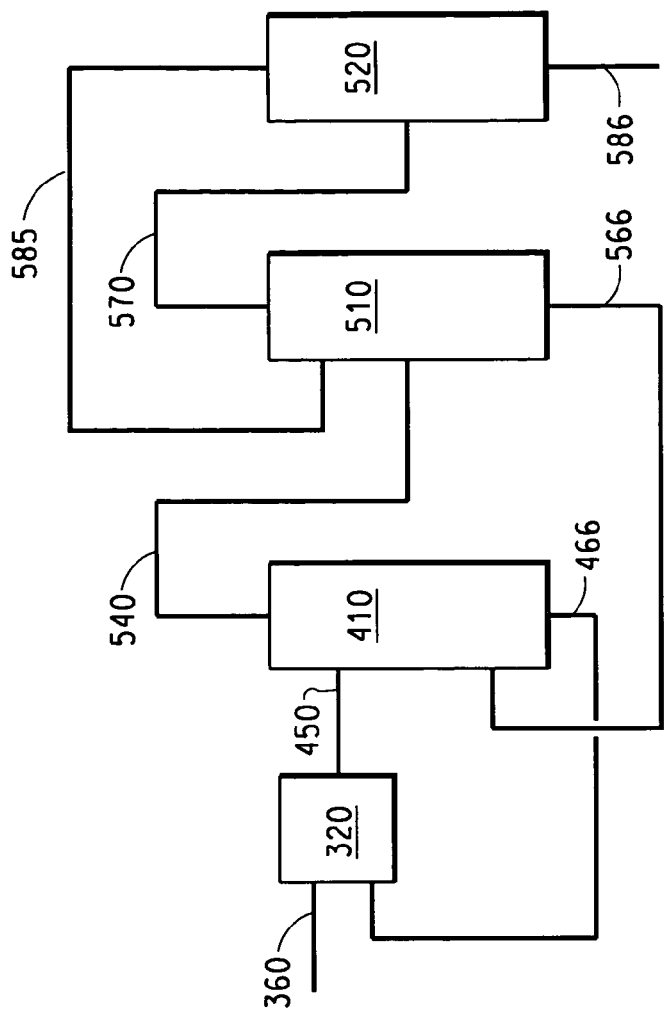
FIG. 2 is a schematic flow diagram illustrating one embodiment for practicing a process for production of Z-HFC-1429.

One aspect relates to compositions containing 1,1,1,3,4,4,5,5,5-nonafluoro-2-pentene (HFC-1429mzy, $CF_3CH=CFCF_2CF_3$) and 1,1,1,2,4,4,5,5,5-nonafluoro-2-pentene (HFC-1429myz, $CF_3CF=CHCF_2CF_3$). HFC-1429mzy and HFC-1429myz, may each exist as one of two configurational isomers, E or Z. Z-HFC-1429myz as used herein, refers to a mixture of the isomers Z-HFC-1429myz and E-HFC-1429myz, wherein the predominant isomer is Z-HFC-1429myz. Z-HFC-1429mzy as used herein, refers to a mixture of the isomers Z-HFC-1429mzy and E-HFC- 1429mzy, wherein the predominant isomer is Z-HFC-1429mzy. "Z-HFC-1429" as used herein refers to a mixture of HFC-1429myz and HFC-1429mzy, wherein both compounds are present predominantly as the Z isomer. Such mixtures of Z-HFC-1429myz and Z-HFC-1429mzy isomers may be prepared by methods known in the art, as described in U.S. Pat. No. 5,268,122, incorporated herein by reference.

As used herein, predominant isomer is intended to mean that isomer which is present in the composition at a concentration of greater than 50 mole percent, preferably greater than 60 mole percent, more preferably greater than 70 mole percent, even more preferably greater than 80 mole percent, and most preferably greater than 90 mole percent.

Anhydrous hydrogen fluoride (HF) is also included in the compositions disclosed herein and is commercially available.

A further aspect relates to compositions containing 1,1,1,2,3,4,4,5,5,5-decafluoropentane (HFC-43-10mee, $CF_3CHFCHFCF_2CF_3$) which may be prepared by methods known in the art, as described in U.S. Pat. No. 5,171,902, incorporated herein by reference, and is available commercially.

In considering a process for the dehydrofluorination of HFC-43-10mee to Z-HFC-1429 and HF and the isolation of Z-HFC-1429 from such a process, it has been discovered surprisingly that the hydrofluoroolefin Z-HFC-1429 forms an azeotrope with HF. Additionally, it has been discovered that the hydrofluorocarbon HFC-43-10mee forms an azeotrope with HF.

One aspect provides a composition, which comprises Z-HFC-1429 and an effective amount of hydrogen fluoride (HF) to form an azeotrope composition. By effective amount is meant an amount, which, when combined with Z-HFC-1429, results in the formation of an azeotrope or near-azeotrope mixture.

A further aspect provides a composition, which comprises HFC-43-10mee and an effective amount of hydrogen fluoride (HF) to form an azeotrope composition. By effective amount is meant an amount, which, when combined with HFC-43-10mee, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near-azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980)19, 432-439). Experimental identification of azeotrope compositions involving the same components may be used to confirm the accuracy of such calculations and/or to modify the calculations at the same or other temperatures and pressures.

Compositions may be formed that comprise azeotrope combinations of hydrogen fluoride with Z-HFC-1429. These include compositions comprising from about 67.4 mole percent to about 88.6 mole percent HF and from about 32.6 mole percent to about 11.4 mole percent Z-HFC-1429 (which forms an azeotrope boiling at a temperature from between about −20° C. and about 100° C. and at a pressure from between about 4.1 psi (28.3 kPa) and about 285 psi (1965 kPa)).

Additionally, near-azeotrope compositions containing HF and Z-HFC-1429 may also be formed. Such near-azeotrope compositions comprise about 10.3 mole percent to about 35.2 mole percent Z-HFC-1429 and about 89.7 mole percent to about 64.8 mole percent HF at temperatures ranging from about −20° C. to about 100° C. and at pressures from about 4.1 psi (28.3 kPa) to about 285 psi (1965 kPa).

Compositions may also be formed that comprise azeotrope combinations of hydrogen fluoride with HFC-43-10mee. These include compositions comprising from about 81.8 mole percent to about 97.3 mole percent HF and from about 18.2 mole percent to about 2.7 mole percent HFC-43-10mee (which forms an azeotrope boiling at a temperature from between about −20° C. and about 100° C. and at a pressure from between about 3.0 psi (20.7 kPa) and about 198 psi (1365 kPa)).

Additionally, near-azeotrope compositions containing HF and HFC-43-10mee may be formed as well. Such near-azeotrope compositions comprise about 2.6 mole percent to about 20.1 mole percent HFC-43-10mee and about 97.4 mole percent to about 79.9 mole percent HF at temperatures ranging from about −20° C. to about 100° C. and at pressures from about 3.0 psi (20.7 kPa) and about 198 psi (1365 kPa).

It should be understood that while an azeotrope or near-azeotrope composition may exist at a particular ratio of the components at given temperatures and pressures, the azeotrope composition may also exist in compositions containing other components.

Compositions may be formed that consist essentially of azeotrope combinations of hydrogen fluoride with Z-HFC-1429. These include compositions consisting essentially of from about 67.4 mole percent to about 88.6 mole percent HF and from about 32.6 mole percent to about 11.4 mole percent Z-HFC-1429 (which forms an azeotrope boiling at a temperature from between about −20° C. and about 100° C. and at a pressure from between about 4.1 psi (28.3 kPa) and about 285 psi (1965 kPa)).

Near-azeotrope compositions may also be formed that consist essentially of about 10.3 mole percent to about 35.2 mole percent Z-HFC-1429 and about 89.7 mole percent to about 64.8 mole percent HF at temperatures ranging from about −20° C. to about 100° C. and at pressures from about 4.1 psi (28.3 kPa) to about 285 psi (1965 kPa).

At atmospheric pressure, the boiling points of hydrofluoric acid and Z-HFC-1429 are about 19.5° C. and 29° C., respectively. The relative volatility at 24 psi (165 kPa) and 20° C. of HF and Z-HFC-1429 was found to be nearly 1.0 as 82.0 mole percent HF and 18.0 mole percent Z-HFC-1429 was approached. The relative volatility at 124 psi (855 kPa) and 70° C. was found to be nearly 1.0 as 73.4 mole percent HF and 26.6 mole percent Z-HFC-1429 was approached. These data indicate that the use of conventional distillation procedures will not result in the separation of a substantially pure compound because of the low value of relative volatility of the compounds.

To determine the relative volatility of HF with Z-HFC-1429, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4$^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and Z-HFC-1429 behave in an ideal manner, and can sufficiently predict the relative volatilities of the components in such mixtures. Thus, the relative volatility becomes nearly 1.0 as 18.0 mole percent Z-HFC-1429 was approached at 20° C. This would make it impossible to separate Z-HFC-1429 from HF by conventional distillation from such a mixture. Where the relative volatility approaches 1.0 defines the system as forming a near-azeotrope or azeotrope composition.

It has been found that azeotropes of Z-HFC-1429 and HF are formed at a variety of temperatures and pressures. Azeotrope compositions may be formed between 4.1 psi (28.3 kPa) (at a temperature of −25° C.) and about 285 psi (1965 kPa) (at a temperature of 100° C.) said compositions consisting essentially of Z-HFC-1429 and HF range from about 67.4 mole percent HF (and 32.6 mole percent Z-HFC-1429) to about 88.6 mole percent HF (and 11.4 mole percent Z-HFC-1429). An azeotrope of HF and Z-HFC-1429 has been found at 20° C. and 24.1 psi (166 kPa) consisting essentially of about 82.0 mole percent HF and about 18.0 mole percent Z-HFC-1429. An azeotrope of HF and Z-HFC-1429 has also been found at 70° C. and 124 psi (855 kPa) consisting essentially of about 73.4 mole percent HF and about 26.6 mole percent Z-HFC-1429. Based upon the above findings, azeotrope compositions at other temperatures and pressures may be calculated. It has been calculated that an azeotrope composition of about 88.6 mole percent HF and about 11.4 mole percent Z-HFC-1429 can be formed at −20° C. and 4.1 psi (28.3 kPa) and an azeotrope composition of about 67.4 mole percent HF and about 32.6 mole percent Z-HFC-1429 can be formed at 100° C. and 285 psi (1965 kPa). Accordingly, one aspect provides an azeotrope composition consisting essentially of from about 67.4 mole percent to about 88.6 mole percent HF and from about 32.6 mole percent to about 11.4 mole percent Z-HFC-1429, said composition having a boiling point of about −20° C. at 4.1 psi (28.3 kPa) to about 100° C. at 285 psi (1965 kPa).

It has also been found that azeotrope or near-azeotrope compositions may be formed between about 3.0 psi (20.7 kPa) to about 198 psi (1365 kPa) at temperatures ranging from about −20° C. to about 100° C., said compositions consisting essentially of about 2.7 mole percent to about 18.2 mole percent HFC-43-10mee and about 97.3 mole percent to about 81.8 mole percent HF.

Compositions may be formed that consist essentially of azeotrope combinations of hydrogen fluoride with HFC-43-10mee. These include compositions consisting essentially of from about 97.3 mole percent to about 81.8 mole percent HF and from about 2.7 mole percent to about 18.2 mole percent HFC-43-10mee (which forms an azeotrope boiling at a temperature from between about −20° C. and about 100° C. and at a pressure from between about 3.0 psi (20.7 kPa) to about 198 psi (1365 kPa)).

Near-azeotrope compositions may also be formed that consist essentially of about 2.6 mole percent to about 20.1 mole percent HFC-43-10mee and about 97.4 mole percent to about 79.9 mole percent HF at temperatures ranging from about −20° C. to about 100° C. and at pressures from about 3.0 psi (20.7 kPa) to about 198 psi (1365 kPa).

At atmospheric pressure, the boiling points of hydrofluoric acid and HFC-43-10mee are about 19.5° C. and 55° C., respectively. The relative volatility at 25 psi (172 kPa) and 30° C. of HF and HFC-43-10mee was found to be nearly 1.0 as 91.9 mole percent HF and 8.1 mole percent HFC-43-10mee was approached. The relative volatility at 117 psi (807 kPa) and 80° C. was found to be nearly 1.0 as 84.8 mole percent HF and 15.2 mole percent HFC-43-10mee was approached. These data indicate that the use of conventional distillation procedures will not result in the separation of a substantially pure compound because of the low value of relative volatility of the compounds.

The "Ptx Method" was also used to determine the relative volatility of HF with HFC-43-10mee. These measurements were then reduced to equilibrium vapor and liquid compositions in the cell by an activity coefficient equation model, the Non-Random, Two-Liquid (NRTL) equation was also used in this case, to represent liquid phase non-idealities.

Without wishing to be bound by any theory or explanation, it is believed that the NRTL equation can sufficiently predict whether or not mixtures of HF and HFC-43-10mee behave in an ideal manner, and can sufficiently predict the relative volatilities of the components in such mixtures. It has been found that the relative volatility becomes nearly 1.0 as 8.1 mole percent HFC-43-10mee was approached at 30° C. This would make it impossible to separate HFC-43-10mee from HF by conventional distillation from such a mixture. Where the relative volatility approaches 1.0 defines the system as forming a near-azeotrope or azeotrope composition.

It has been found that azeotropes of HFC-43-10mee and HF are formed at a variety of temperatures and pressures. Azeotrope compositions may be formed between 3.0 psi (20.7 kPa) (at a temperature of −20° C.) and about 198 psi (1365 kPa) (at a temperature of 100° C.) said compositions consisting essentially of HFC-43-10mee and HF ranging from about 97.3 mole percent HF (and 2.7 mole percent HFC-43-10mee) to about 81.8 mole percent HF (and 18.2 mole percent HFC-43-10mee). An azeotrope of HF and HFC-43-10mee has been found at 30° C. and 25 psi (172 kPa) consisting essentially of about 91.9 mole percent HF and about 8.1 mole percent HFC-43-10mee. An azeotrope of HF and HFC-43-10mee has also been found at 79.8° C. and 117 psi (807 kPa) consisting essentially of about 84.8 mole percent HF and about 15.2 mole percent HFC-43-10mee. Based upon the above findings, azeotrope compositions at other temperatures and pressures may be calculated. It has been calculated that an azeotrope composition of about 97.3 mole percent HF and about 2.7 mole percent HFC-43-10mee can be formed at −20° C. and 3.0 psi (20.7 kPa) and an azeotrope composition of about 81.8 mole percent HF and about 18.2 mole percent HFC-43-10mee can be formed at 100° C. and 198 psi (1365 kPa). Accordingly, one aspect provides an azeotrope composition consisting essentially of from about 81.8 mole percent to about 97.3 mole percent HF and from about 18.2 mole percent to about 2.7 mole percent HFC-43-10mee, said composition having a boiling point of about −20° C. at 3 psi (20.7 kPa) to about 100° C. at 198 psi (1365 kPa).

It has also been found that azeotrope or near-azeotrope compositions may be formed between about 3.0 psi (20.7 kPa) to about 198 psi (1365 kPa) at temperatures ranging from about −20° C. to about 100° C., said compositions consisting essentially of about 2.6 mole percent to about 20.1 mole percent HFC-43-10mee and about 97.4 mole percent to about 79.9 mole percent HF.

The HF/Z-HFC-1429 azeotrope and near-azeotrope compositions and the HF/HFC-43-10mee azeotrope and near-azeotrope compositions are useful in processes to produce Z-HFC-1429, in processes to purify Z-HFC-1429, and in processes to purify HFC-43-10mee. In fact, the HF/Z-HFC-1429 azeotrope and near-azeotrope compositions may be useful in any process that creates a composition containing Z-HFC-1429 and HF. And HF/HFC-43-10mee azeotrope and near-azeotrope compositions may be useful in any process that creates a composition containing HFC-43-10mee and HF.

Azeotropic distillation may be carried out to separate Z-HFC-1429 from HFC-43-10mee, which is the starting material for production of Z-HFC-1429, by vapor phase dehydrofluorination. A two-column azeotropic distillation may then be carried out to separate the co-produced HF from the desired Z-HFC-1429 product. And another two-column azeotropic distillation may be carried out to separate HF from HFC-43-10mee. HF may be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes utilizing HF from such product mixtures.

While the initial mixture treated in accordance with the processes disclosed herein can be obtained from a variety of sources, including by adding Z-HFC-1429 to HF-containing compositions, an advantageous use of the present processes resides in treating the effluent mixtures from the preparation of Z-HFC-1429.

Z-HFC-1429 may be prepared by the vapor phase dehydrofluorination of HFC-43-10mee by processes known in the art, such as those described in U.S. Pat. No. 5,268,122, incorporated herein by reference.

A further aspect provides a process for the separation of Z-HFC-1429 from HFC-43-10mee comprising: a) forming a mixture of Z-HFC-1429, HFC-43-10mee, and hydrogen fluoride; and b) subjecting said mixture to a distillation step from which is formed a column distillate composition comprising an azeotrope or near-azeotrope composition of HF and Z-HFC-1429 essentially free of HFC-43-10mee.

As described herein, by "essentially free of HFC-43-10mee" is meant that the composition contains less than about 100 ppm (mole basis), preferably less than about 10 ppm and most preferably less than about 1 ppm, of HFC-43-10mee.

This azeotropic distillation takes advantage of the low boiling azeotrope composition formed by Z-HFC-1429 and HF. The azeotrope composition boils at a temperature lower than the boiling point of either pure component and lower than the boiling point of HFC-43-10mee as well.

As stated previously, the mixture of Z-HFC-1429, HFC-43-10mee and HF may be formed by any practical means. Generally, the present process is particularly useful for the separation of Z-HFC-1429 from the reaction mixture produced by the dehydrofluorination of HFC-43-10mee. HF is a co-product formed in this dehydrofluorination reaction. The reaction mixture produced may then be treated by the instant process to remove HFC-43-10mee. The Z-HFC-1429 is taken overhead as the distillate from the distillation column as an azeotrope or near-azeotrope composition of Z-HFC-1429 with HF. The HFC-43-10mee is taken out of the bottom of the column as a bottoms composition and may contain some amount of Z-HFC-1429, as well. The amount of Z-HFC-1429 in the HFC-43-10mee from the bottom of the distillation column may vary from about 45 mole percent to about 1 part per million (ppm, mole basis) depending on the manner in which the dehydrofluorination reaction is conducted.

The column bottoms composition comprising HFC-43-10mee and Z-HFC-1429 may be distilled using, for example, standard distillation techniques to separate the two components. However, it is preferred that the azeotropic distillation be conducted in such a manner as to produce a column bottoms composition comprising HFC-43-10mee essentially free of Z-HFC-1429.

In one embodiment, operating the present azeotropic distillation involves modifying the distillation parameters to send not only the Z-HFC-1429/HF azeotrope overhead, but also send any excess Z-HFC-1429 overhead as well (this would be Z-HFC-1429 above the azeotrope concentration). If the appropriate conditions are utilized, then all the Z-HFC-1429 will go overhead with the HF. Thus, the HFC-43-10mee removed from the column bottoms will be essentially free of Z-HFC-1429.

As described herein, by "essentially free of Z-HFC-1429" is meant that the composition contains less than about 100 ppm (mole basis), preferably less than about 10 ppm and most preferably less than about 1 ppm, of Z-HFC-1429.

In the distillation step, the distillate exiting the distillation column overhead comprising HF and Z-HFC-1429 may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 15 psi (103 kPa) to about 50 psi (345 kPa). The distillation column is typically operated at a pressure of about 20 psi (138 kPa) with a bottoms temperature from about 45° C. to about 70° C. and a tops temperature from about 15° C. to about 40° C. Normally, increasing the reflux ratio results in increased distillate stream purity, but generally the reflux ratio ranges between 0.2/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of HF and Z-HFC-1429, essentially free of HFC-43-10mee, may be treated to remove the HF and provide pure Z-HFC-1429 as product. This may be accomplished, for example, by neutralization or by a second distillation process, as described herein.

A further aspect provides a process for the separation of Z-HFC-1429 from a mixture comprising an azeotrope or near-azeotrope composition of Z-HFC-1429 and HF, said process comprising: a) subjecting said mixture to a first distillation step in which a composition enriched in either (i) hydrogen fluoride or (ii) Z-HFC-1429 is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with the bottoms composition enriched in the same component which was enriched in the first distillation composition.

The process as described above takes advantage of the change in azeotrope composition at different pressures to effectuate the separation of Z-HFC-1429 and HF. The first distillation step may be carried out at high pressure relative to the second distillation step. At higher pressures, the HF/Z-HFC-1429 azeotrope contains higher levels of Z-HFC-1429. Thus, this high-pressure distillation step produces an excess of hydrogen fluoride, which boiling at a higher temperature than the azeotrope will exit the column as the bottoms as pure hydrogen fluoride. The first column distillate is then fed to a second distillation step operating at lower pressure. At the lower pressure, the HF/Z-HFC-1429 azeotrope shifts to lower concentrations of Z-HFC-1429. Therefore, in this second distillation step, there exists an excess of Z-HFC-1429. The excess Z-HFC-1429, having a boiling point higher than the azeotrope, exits the second distillation column as the bottoms composition.

Alternatively, the first distillation step may be carried out at low pressure relative to the second distillation step. At lower pressures, the HF/Z-HFC-1429 azeotrope contains higher levels of HF. Thus, this low-pressure distillation step produces an excess of Z-HFC-1429, which boiling at a higher temperature than the azeotrope, will exit the column as the bottoms as pure Z-HFC-1429. The first column distillate is then fed to a second distillation step operating at higher pressure. At the higher pressure, the HF/Z-HFC-1429 azeotrope shifts to lower concentrations of hydrogen fluoride. Therefore, in this second distillation step there exists an excess of hydrogen fluoride. The excess hydrogen fluoride will exit the second distillation column as the bottoms composition.

The endothermic dehydrofluorination reaction of HFC-43-10mee to produce Z-HFC-1429 may be accomplished, for example, in a tubular reactor with catalyst in the tubes and with a heating medium on the shellside of the reactor. Alternatively, a heat carrier may be used to permit adiabatic operation. Either pure HFC-43-10mee or pure Z-HFC-1429, both being produced by the distillation processes described herein, may be recycled back to the reactor to serve as heat carrier. HFC-43-10mee would be a preferred heat carrier, as introduction of Z-HFC-1429 to the dehydrofluorination reactor will result in a reduction in single-pass conversion of HFC-43-10mee.

In both the first and second distillation steps, the distillate exiting the distillation column overhead comprising HF and Z-HFC-1429 may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation steps depend upon a number of parameters, such as the diameter of the distillation column, feed points, and the number of separation stages in the column, among others. The operating pressure of the high pressure distillation column (whether high pressure is the first distillation column or the second distillation column) may range from about 50 psi (345 kPa) pressure to about 300 psi (2068 kPa), normally about 100 psi (690 kPa) to about 250 psi (1724 kPa). The high pressure distillation column is typically operated at a pressure of about 225 psi (1551 kPa) with a bottoms temperature of about 117° C. and a tops temperature of about 92° C. Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the low pressure distillation column (whether low pressure is the first distillation column or the second distillation column) may range from about 5 psi (34 kPa) pressure to about 50 psi (345 kPa), normally about 10 psi (69 kPa) to about 25 psi (172 kPa). The low pressure distillation column is typically operated at a pressure of about 20 psi (138 kPa) with a bottoms temperature of about 40° C. and a tops temperature of about 15° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

Figure 1:
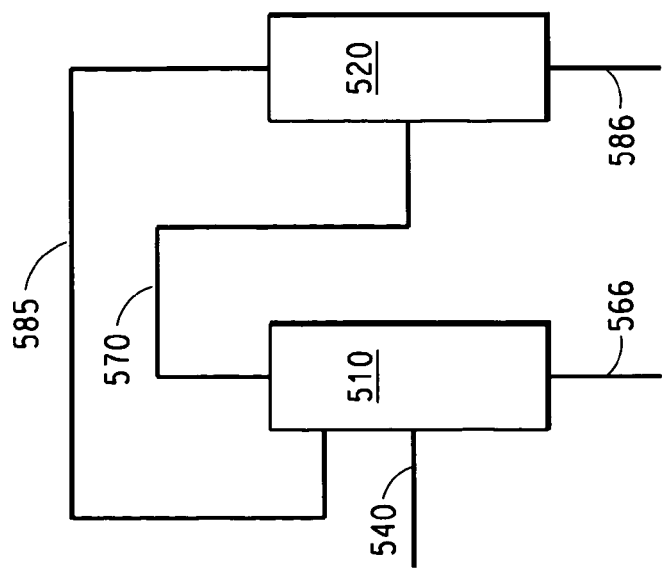
FIG. 1 is a schematic flow diagram illustrating one embodiment for practicing a two-column azeotropic distillation process.

FIG. 1 is illustrative of one embodiment for practicing the present two-column distillation process for the separation of Z-HFC-1429 and HF. Referring to FIG. 1, a feed mixture derived from a prior azeotropic distillation comprising HF and Z-HFC-1429, wherein the molar ratio of HF:Z-HFC-1429 is about 4.0:1 (or higher), is passed through line (540) to a multiple stage distillation column (510), operating at a temperature of about 90° C. and a pressure of about 225 psi (1550 kPa). The bottoms of the distillation column (510), containing essentially pure hydrogen fluoride at a temperature of about 118° C. and a pressure of about 227 psi (1565 kPa) is removed from the bottom of column (510) through line (566). The distillate from column (510), containing the HF/Z-HFC-1429 azeotrope (HF:Z-HFC-1429 molar ratio is about 2.3:1) at a temperature of about 92° C. and a pressure of about 225 psi (1550 kPa) is removed from the top of column (510) and sent through line (570) to a multiple stage distillation column (520). The distillate from column (520), containing the HF/Z-HFC-1429 azeotrope (molar ratio is about 4.7:1) at a temperature of about 15° C. and a pressure of about 20 psi (138 kPa), is removed from column (520) through line (585) and is recycled back to column (510). The bottoms of column (520) containing essentially pure HF at a temperature of about 40° C. and a pressure of about 22 psi (152 kPa) is removed through line (586).

In another embodiment, the pressures of the columns are reversed. Again referring to FIG. 1, feed mixture derived from a prior azeotropic distillation comprising HF and Z-HFC-1429, wherein the molar ratio of HF:Z-HFC-1429 is about 1.4:1 (or lower), is passed through line (540) to a multiple stage distillation column (510), operating at a temperature of about 15° C. and a pressure of about 20 psi (138 kPa). The bottoms of the distillation column (510), containing essentially pure Z-HFC-1429 at a temperature of about 40° C. and a pressure of about 22 psi (152 kPa) is removed from the bottom of column (510) through line (566). The distillate from column (510), containing the HF/Z-HFC-1429 azeotrope (HF:Z-HFC-1429 molar ratio is about 4.7:1) at a temperature of about 15° C. and a pressure of about 20 psi (138 kPa) is removed from the top of column (510) and sent through line (570) to a multiple stage distillation column (520). The distillate from column (520), containing the HF/Z-HFC-1429 azeotrope (molar ratio is about 2.3:1) at a temperature of about 92° C. and a pressure of about 225 psi (1550 kPa), is removed from column (520) through line (585) and is recycled back to column (510). The bottoms of column (520) containing essentially pure HF at a temperature of about 118° C. and a pressure of about 227 psi (1565 kPa) is removed through line (586).

A further aspect provides a process for the separation of HFC-43-10mee from a mixture comprising an azeotrope or near-azeotrope composition of HFC-43-10mee and hydrogen fluoride, said process comprising: a) subjecting said mixture to a first distillation step in which a composition enriched in either (i) hydrogen fluoride or (ii) HFC-43-10mee is removed as a first distillate composition with a first bottoms composition being enriched in the other of said components (i) or (ii); and b) subjecting said first distillate composition to a second distillation step conducted at a different pressure than the first distillation step in which the component enriched in the first bottoms composition in (a) is removed in a second distillate composition with a second bottoms composition enriched in the same component which was enriched in the first distillate composition.

Similar to the previously described two-column azeotropic distillation, for both the first and second distillation steps, the distillate exiting the distillation column overhead comprising HF and HFC-43-10mee may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the high pressure distillation column (whether high pressure is the first distillation column or the second distillation column) may range from about 50 psi (345 kPa) pressure to about 200 psi (1380 kPa), normally about 100 psi (70 kPa) to about 200 psi (1380 kPa). The high pressure distillation column is typically operated at a pressure of about 185 psi (1276 kPa) with a bottoms temperature of about 109° C. and a tops temperature of about 98° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the low pressure distillation column (whether low pressure is the first distillation column or the second distillation column) may range from about 10 psi (69 kPa) pressure to about 100 psi (689 kPa), normally about 15 psi (103 kPa) to about 50 psi (345 kPa). The low pressure distillation column is typically operated at a pressure of about 20 psi (138 kPa) with a bottoms temperature of about 66° C. and a tops temperature of about 24° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

FIG. 1 is also illustrative of one embodiment for practicing the present two-column distillation process for separation of HFC-43-10mee and HF. Referring to FIG. 1, a feed mixture comprising an azeotrope or near-azeotrope composition of HFC-43-10mee and HF, wherein the molar ratio of HF:HFC-43-10mee is about 0.53:1 (or lower), is passed through line (540) to a multiple stage distillation column (510), operating at a temperature of about 24° C. and a pressure of about 20 psi (138 kPa). The bottoms of the distillation column (510), containing essentially pure HFC-43-10mee at a temperature of about 66° C. and a pressure of about 22 psi (152 kPa) is removed from the bottom of column (510) through line (566). The distillate from column (510), containing the HF/HFC-43-10mee azeotrope (HF:HFC-43-10mee molar ratio is about 12.4:1) at a temperature of about 24° C. and a pressure of about 20 psi (138 kPa) is removed from the top of column (510) and sent through line (570) to a multiple stage distillation column (520). The distillate from column (520), containing the HF/HFC-43-10mee azeotrope (molar ratio is about 4.9:1) at a temperature of about 98° C. and a pressure of about 185 psi (1276 kPa), is removed from column (520) through line (585) and is recycled back to column (510). The bottoms of column (520) containing essentially pure hydrogen fluoride at a temperature of about 109° C. and a pressure of about 187 psi (1289 kPa) is removed through line (586).

In another embodiment, the pressures of the columns are reversed. Again referring to FIG. 1, a feed mixture comprising an azeotrope or near-azeotrope composition of HFC-43-10mee and HF, wherein the molar ratio of HF:HFC-43-10mee is about 5.1:1 (or higher), is passed through line (540) to a multiple stage distillation column (510), operating at a temperature of about 97° C. and a pressure of about 185 psi (1276 kPa). The bottoms of the distillation column (510), containing essentially pure hydrogen fluoride at a temperature of about 109° C. and a pressure of about 187 psi (1289 kPa) is removed from the bottom of column (510) through line (566). The distillate from column (510), containing the HF/HFC-43-10mee azeotrope (HF:HFC-43-10mee molar ratio is about 4.9:1) at a temperature of about 98° C. and a pressure of about 185 psi (1276 kPa) is removed from the top of column (510) and sent through line (570) to a multiple stage distillation column (520). The distillate from column (520), containing the HF/HFC-43-10mee azeotrope (molar ratio is about 12.3:1) at a temperature of about 24° C. and a pressure of about 20 psi (138 kPa), is removed from column (520) through line (585) and is recycled back to column (510). The bottoms of column (520) containing essentially pure HFC-43-10mee at a temperature of about 66° C. and a pressure of about 22 psi (152 kPa) is removed through line (586).

A further aspect provides a process for the purification of Z-HFC-1429 from a mixture of Z-HFC-1429, HFC-43-10mee, and HF, said process comprising: a) subjecting said mixture to a first distillation step to form a first distillate comprising an azeotrope or near-azeotrope composition containing Z-HFC-1429 and HF and a first bottoms comprising HFC-43-10mee; b) subjecting said first distillate to a second distillation step from which a composition enriched in either (i) hydrogen fluoride or (ii) HFC-43-10mee is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

A further aspect provides a process to produce Z-HFC-1429 comprising: a) feeding HFC-43-10mee to a reaction zone for dehydrofluorination to form a reaction product composition comprising Z-HFC-1429, unreacted HFC-43-10mee and hydrogen fluoride; b) subjecting said reaction product composition to a first distillation step to form a first distillate composition comprising an azeotrope or near-azeotrope composition containing Z-HFC-1429 and HF and a first bottoms composition comprising HFC-43-10mee; c) subjecting said first distillate composition to a second distillation step from which a composition enriched in either (i) hydrogen fluoride or (ii) HFC-43-10mee is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (b) is removed in a third distillate composition with a third bottoms composition enriched in the same component that was enriched in the first distillation composition. Optionally, the process may further comprise recycling at least some portion of said first bottoms composition to said reaction zone. Optionally, the process may further comprise recycling at least some portion of said second bottoms composition or said third bottoms composition to said reaction zone. Optionally, the process may further comprise recycling at least some portion of said second bottoms composition or said third bottoms composition to said first distillation step. Optionally, the process may further comprise recovering at least some portion of said second bottoms composition or third bottoms composition as Z-HFC-1429 essentially free of HFC-43-10mee and HF.

As described herein, by "essentially free of HFC-43-10mee and HF" is meant that the composition contains less than about 100 ppm (mole basis), preferably less than about 10 ppm and most preferably less than about 1 ppm, of each of HFC-43-10mee and HF.

The reaction zone for the dehydrofluorination may comprise a flow reactor preferably containing a fixed bed of dehydrofluorination catalyst. The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

FIG. 2 is illustrative of one embodiment for practicing the present process for production of Z-HFC-1429. HFC-43-10mee is fed through line (360) to reactor (320). The reactor effluent mixture comprising HF, HFC-43-10mee and Z-HFC-1429, exits the reactor through line (450) and is fed to a multiple stage distillation column (410). The bottoms of distillation column (410), containing essentially pure HFC-43-10mee is removed from the bottom of column (410) through line (466) and may be recycled back to the reactor. The distillate from column (410), containing the HF/Z-HFC-1429 azeotrope is removed from the top of column (410) and is sent through line (540) to a second multiple stage distillation column (510). The bottoms from column (510), which is essentially pure Z-HFC-1429, is removed from column (510) through line (566) and may be recycled back to the reactor (320) as a heat carrier. The distillate from column (510), containing the HF/Z-HFC-1429 azeotrope, is fed through line (570) to a third multiple stage distillation column (520). The distillate from column (520) comprising HF/Z-HFC-1429 is removed through line (585) and may be recycled to the second distillation column (510). The bottoms composition from column (520) is essentially pure HF and is removed from column (520) through line (586). The essentially pure HF product from this process may be used in any manner appropriate such as feeding to a fluorination reactor for production of a fluorochemical compound, or may be neutralized for disposal.

While not illustrated in the figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column that it is fed. Therefore, heating or cooling of the process stream may be necessary to match the temperature.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Dehydrofluorination of HFC-43-10mee to HFC-1492mzy and HFC-1429myz Over Carbonaceous Catalyst To a Hastelloy nickel alloy reactor (1.0" OD×0.854" ID×9.5" L) was charged 14.32 g (25 mL) of spherical (8 mesh) three dimensional matrix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple, positioned between the reactor wall and the heater measured the reactor temperature. After charging the reactor with the carbonaceous material, nitrogen (10 mL/min) was passed through the reactor and the temperature was raised to 200° C. during a period of one hour and maintained at this temperature for an additional 4 hours. The reactor temperature was then raised to the desired operating temperature and a flow of HFC-43-10mee (at 5 mL/hour) and nitrogen was started through the reactor.

A portion of the total reactor effluent was sampled on-line for organic product analysis using a gas chromatograph equipped with a mass selective detector (GC-MS). The bulk of the reactor effluent containing organic products and also inorganic acid, such as HF, was treated with aqueous caustic for neutralization.

Results obtained in GC mole percent are summarized in Table 1. In the table, temp is temperature, unks is unknowns, and other HFCs include HFC-23 (trifluoromethane), HFC-125 (pentafluoroethane) and HFC-134a (1,1,1,2-tetrafluoroethane).

TABLE 1

| Reactor temp, °C. | $N_2$ flow, sccm | Unks | Mole Percent | | | | | |
|---|---|---|---|---|---|---|---|---|
| | | | Z-HFC-1429 myz | Z-HFC-1429 mzy | Other HFC-1429 | HFC-43-10mee | Other HFC-43-10s | Other HFCs |
| 200 | 20 | 1.47 | 12.9 | 29.6 | 0.36 | 55.0 | 0.65 | 0.08 |
| 200 | 20 | 2.05 | 10.7 | 24.3 | 0.29 | 62.1 | 0.47 | 0.09 |
| 250 | 20 | 2.24 | 28.1 | 59.6 | 1.30 | 1.01 | 7.43 | 0.09 |
| 250 | 20 | 2.07 | 28.1 | 59.9 | 1.30 | 1.00 | 7.35 | 0.33 |
| 250 | 40 | 2.14 | 28.9 | 60.2 | 1.35 | 0.90 | 6.25 | 0.32 |

Example 2

Phase Studies of Mixtures of HF and Z-HFC-1429

A phase study was performed for a composition consisting essentially of Z-HFC-1429 and HF, wherein the composition was varied and the vapor pressures were measured at both 20° C. and 70° C. Based upon the data from the phase studies, azeotrope compositions at other temperature and pressures have been calculated.

Table 2 provides a compilation of experimental and calculated azeotrope compositions for HF and Z-HFC-1429 at specified temperatures and pressures.

TABLE 2

| Temperature, °C. | Pressure, psi (kPa) | Mole % HF | Mole % Z-HFC-1429 |
|---|---|---|---|
| −20 | 4.1 (28.3) | 88.6 | 11.4 |
| −15 | 5.3 (36.5) | 87.8 | 12.2 |
| −10 | 6.7 (46.2) | 87.0 | 13.0 |
| −5 | 8.5 (58.6) | 86.2 | 13.8 |
| 0 | 10.6 (73.1) | 85.3 | 14.7 |
| 20 | 24.2 (167) | 82.0 | 18.0 |
| 40 | 49.3 (340) | 78.6 | 21.4 |
| 60 | 92.8 (639) | 75.1 | 24.9 |
| 65 | 108 (742) | 74.2 | 25.8 |
| 70 | 124 (855) | 73.4 | 26.6 |
| 75 | 143 (988) | 72.5 | 27.5 |
| 80 | 165 (1136) | 71.6 | 28.4 |
| 85 | 189 (1300) | 70.6 | 29.4 |
| 90 | 217 (1495) | 69.7 | 30.3 |
| 95 | 248 (1713) | 68.6 | 31.4 |
| 100 | 285 (1965) | 67.4 | 32.6 |

Example 3

Dew Point and Bubble Point Vapor Pressures for Z-HFC-1429

The dew point and bubble point vapor pressures for compositions disclosed herein were calculated from measured and claculated thermodynamic properties. The near-azeotrope range is indicated by the minimum and maximum concentration of Z-HFC-1429 (mole percent, mol %) for which the difference in dew point and bubble point pressures is less than or equal to 3% (based upon bubble point pressure). The results are summarized in Table 3.

TABLE 3

| Temperature, °C. | Azeotrope composition, mol % Z-HFC-1429 | Near-azeotrope compositions, mol % Z-HFC-1429 | |
|---|---|---|---|
| | | Minimum | Maximum |
| −20 | 11.4 | 10.3 | 12.4 |
| 0 | 14.7 | 13.4 | 16.0 |
| 20 | 18.0 | 16.6 | 19.7 |
| 70 | 26.6 | 24.9 | 29.2 |
| 100 | 32.6 | 30.7 | 35.2 |

Example 4

Phase Studies of Mixtures of HF and HFC-43-10mee

A phase study was performed for a composition consisting essentially of HFC-43-10mee and HF, wherein the composition was varied and the vapor pressures were measured at both 30° C. and 80° C. Based upon the data from the phase studies, azeotrope compositions at other temperature and pressures have been calculated.

Table 4 provides a compilation of experimental and calculated azeotrope compositions for HF and HFC-43-10mee at specified temperatures and pressures.

TABLE 4

| Temperature, °C. | Pressure, psi (kPa) | Mole % HF | Mole % HFC-43-10mee |
|---|---|---|---|
| −20 | 3.0 (20.7) | 97.3 | 2.7 |
| 0 | 7.7 (53.1) | 95.5 | 4.5 |
| 20 | 17.3 (119) | 93.2 | 6.8 |
| 30 | 25.0 (172) | 91.9 | 8.1 |
| 39.5 | 34.7 (239) | 90.7 | 9.3 |
| 40 | 35.3 (243) | 90.6 | 9.4 |
| 60 | 66.6 (459) | 87.8 | 12.2 |
| 65 | 77.3 (533) | 87.0 | 13.0 |
| 70 | 89.3 (616) | 86.3 | 13.7 |
| 75 | 103 (710) | 85.5 | 14.5 |
| 80 | 118 (814) | 84.8 | 15.2 |
| 85 | 135 (931) | 84.0 | 16.0 |

TABLE 4-continued

| Temperature, °C. | Pressure, psi (kPa) | Mole % HF | Mole % HFC-43-10mee |
|---|---|---|---|
| 90 | 154 (1062) | 83.3 | 16.7 |
| 95 | 175 (1207) | 82.6 | 72.4 |
| 97.2 | 185 (1276) | 82.2 | 17.8 |
| 100 | 198 (1365) | 81.8 | 18.2 |

Example 5

Dew Point and Bubble Point Vapor Pressures for HFC-43-10mee

The dew point and bubble point vapor pressures for compositions disclosed herein were calculated from measured and calculated thermodynamic properties. The near-azeotrope range is indicated by the minimum and maximum concentration of HFC-43-10mee (mole percent, mol %) for which the difference in dew point and bubble point pressures is less than or equal to 3% (based upon bubble point pressure). The results are summarized in Table 5.

TABLE 5

| Temperature, °C. | Azeotrope composition, mol % HFC-43-10mee | Near-azeotrope compositions, mol % HFC-43-10mee | |
|---|---|---|---|
| | | Minimum | Maximum |
| −20 | 2.7 | 2.6 | 2.9 |
| 0 | 4.6 | 2.8 | 4.8 |
| 20 | 6.8 | 4.9 | 7.3 |
| 70 | 13.7 | 11.2 | 15.0 |
| 100 | 18.2 | 15.0 | 20.1 |

Example 6

Azeotropic Distillation for Separation of Z-HFC-1429 from HFC-43-10mee

A mixture of HF, Z-HFC-1429, and HFC-43-10mee is fed to a distillation column for the purpose of purification of Z-HFC-1429. The data in Table 6 were obtained by calculation using measured and calculated thermodynamic properties.

TABLE 6

| Component or variable | Column feed | Column overhead (distillate) | Column bottoms |
|---|---|---|---|
| HFC-43-10mee, mol % | 33.4 | 1 ppm | 44.1 |
| Z-HFC-1429, mol % | 33.3 | 17.4 | 55.9 |
| HF, mol % | 33.3 | 82.6 | — |
| Temp, °C. | — | 22.6 | 51.2 |
| Pressure, psi (kPa) | — | 19.7 (136) | |

Example 7

Azeotropic Distillation for Separation of Z-HFC-1429 from HFC-43-10mee

A mixture of HF, Z-HFC-1429, and HFC-43-10mee is fed to a distillation column for the purpose of purification of Z-HFC-1429. The data in Table 7 were obtained by calculation using measured and calculated thermodynamic properties.

TABLE 7

| Component or variable | Column feed | Column overhead (distillate) | Column bottoms |
|---|---|---|---|
| HFC-43-10mee, mol % | 33.4 | 1 ppm | 100 |
| Z-HFC-1429, mol % | 33.3 | 50.0 | 2 ppm |
| HF, mol % | 33.3 | 50.0 | — |
| Temp, °C. | — | 30.0 | 21.8 |
| Pressure, psi (kPa) | — | 19.7 (136) | 21.7 (150) |

Example 8

Two-Column Azeotropic Distillation for Separation of Z-HFC-1429 from HF

A mixture of HF and Z-HFC-1429 is fed to a distillation process for the purpose of purification of the Z-HFC-1429. The data in Table 8 were obtained by calculation using measured and calculated thermodynamic properties. The numbers at the top of the columns refer to FIG. 1.

TABLE 8

| Compound or variable | 540 Feed Mixture | 570 Column (510) distillate | 566 HF product | 585 Column (520) distillate | 586 Z-HFC-1429 product |
|---|---|---|---|---|---|
| HF, mol % | 17.4 | 70.0 | 100 | 82.5 | 100 |
| Z-HFC-1429, mol % | 82.6 | 30.0 | — | 17.5 | — |
| Temp., °C. | — | 91.7 | 117.5 | 14.9 | 39.8 |
| Pres., psi (kPa) | — | 224.7 (1549) | 226.7 (1563) | 19.7 (136) | 21.7 (150) |

Example 9

Two-Column Azeotropic Distillation for Separation of Z-HFC-1429 from HF

A mixture of HF and Z-HFC-1429 is fed to a distillation process for the purpose of purification of the Z-HFC-1429. The data in Table 9 were obtained by calculation using measured and calculated thermodynamic properties. The numbers at the top of the columns refer to FIG. 1.

TABLE 9

| Compound or variable | 540 Feed Mixture | 570 Column (510) distillate | 566 Z-HFC-1429 product | 585 Column (520) distillate | 586 HF product |
|---|---|---|---|---|---|
| HF, mol % | 75.9 | 82.5 | — | 70.0 | 100 |
| Z-HFC-1429, mol % | 24.1 | 17.5 | 100 | 30.0 | — |
| Temp., ° C. | — | 14.9 | 39.8 | 91.7 | 117.5 |
| Pres., psi (kPa) | — | 19.7 (136) | 21.7 (150) | 224.7 (1549) | 226.7 (1563) |

Example 10

Two-Column Azeotropic Distillation for Separation of Z-HFC-1429 from HF

A mixture of HF and Z-HFC-1429 is fed to a distillation process for the purpose of purification of the Z-HFC-1429. The data in Table 10 were obtained by calculation using measured and calculated thermodynamic properties. The numbers at the top of the columns refer to FIG. 1.

TABLE 10

| Compound or variable | 540 Feed Mixture | 570 Column (510) distillate | 566 Z-HFC-1429 product | 585 Column (520) distillate | 586 HF product |
|---|---|---|---|---|---|
| HF, mol % | 58.2 | 82.5 | — | 70.0 | 100 |
| Z-HFC-1429, mol % | 41.8 | 17.5 | 100 | 30.0 | — |
| Temp., ° C. | — | 14.9 | 39.8 | 91.7 | 117.5 |
| Pres., psi (kPa) | — | 19.7 (136) | 21.7 (150) | 224.7 (1549) | 226.7 (1563) |

Example 11

Two-Column Azeotropic Distillation for Separation of Z-HFC-1429 from HF

A mixture of HF and Z-HFC-1429 is fed to a distillation process for the purpose of purification of the Z-HFC-1429. The data in Table 11 were obtained by calculation using measured and calculated thermodynamic properties. The numbers at the top of the columns refer to FIG. 1.

TABLE 11

| Compound or variable | 540 Feed Mixture | 570 Column (510) distillate | 566 HF product | 585 Column (520) distillate | 586 Z-HFC-1429 product |
|---|---|---|---|---|---|
| HF, mol % | 73.9 | 70.0 | 100 | 82.5 | 100 |
| Z-HFC-1429, mol % | 26.1 | 30.0 | — | 17.5 | — |
| Temp., ° C. | — | 91.7 | 117.5 | 14.9 | 39.8 |
| Pres., psi (kPa) | — | 224.7 (1549) | 226.7 (1563) | 19.7 (136) | 21.7 (150) |

Example 12

Two-Column Azeotropic Distillation for Separation of HFC-43-10mee from HF

A mixture of HF and HFC-43-10mee is fed to a distillation process for the purpose of purification of the HFC-43-10mee. The data in Table 12 were obtained by calculation using measured and calculated thermodynamic properties. The numbers at the top of the columns refer to FIG. 1.

TABLE 12

| Compound or variable | 540 Feed Mixture | 570 Column (510) distillate | 566 HF product | 585 Column (520) distillate | 586 HFC-43-10mee product |
|---|---|---|---|---|---|
| HF, mol % | 87.0 | 83.0 | 100 | 92.5 | 100 |
| HFC-43-10mee, mol % | 13.0 | 17.0 | — | 7.5 | — |
| Temp., °C. | — | 97.5 | 109 | 23.8 | 65.8 |
| Pres., psi (kPa) | — | 184.7 (1273) | 186.7 (1287) | 19.7 (136) | 21.7 (150) |

Example 13

Two-Column Azeotropic Distillation for Separation of HFC-43-10mee from HF

A mixture of HF and HFC-43-10mee is fed to a distillation process for the purpose of purification of the HFC-43-10mee. The data in Table 13 were obtained by calculation using measured and calculated thermodynamic properties. The numbers at the top of the columns refer to FIG. 1.

TABLE 13

| Compound or variable | 540 Feed Mixture | 570 Column (510) distillate | 566 HFC-43-10mee product | 585 Column (520) distillate | 586 HF product |
|---|---|---|---|---|---|
| HF, mol % | 34.6 | 92.5 | 100 | 83.0 | 100 |
| HFC-43-10mee, mol % | 65.4 | 7.5 | — | 17.0 | — |
| Temp., °C. | — | 23.8 | 65.8 | 97.5 | 109 |
| Pres., psi (kPa) | — | 19.7 (136) | 21.7 (150) | 184.7 (1273) | 186.7 (1287) |

Example 14

Two-Column Azeotropic Distillation for Separation of HFC-43-10mee from HF

A mixture of HF and HFC-43-10mee is fed to a distillation process for the purpose of purification of the HFC-43-10mee. The data in Table 14 were obtained by calculation using measured and calculated thermodynamic properties. The numbers at the top of the columns refer to FIG. 1.

TABLE 14

| Compound or variable | 540 Feed Mixture | 570 Column (510) distillate | 566 HFC-43-10mee product | 585 Column (520) distillate | 586 HF product |
|---|---|---|---|---|---|
| HF, mol % | 78.0 | 92.5 | 100 | 83.0 | 100 |
| HFC-43-10mee, mol % | 22.0 | 7.5 | — | 17.0 | — |

Example 15

Two-Column Azeotropic Distillation for Separation of HFC-43-10mee from HF

A mixture of HF and HFC-43-10mee is fed to a distillation process for the purpose of purification of the HFC-43-10mee. The data in Table 15 were obtained by calculation using measured and calculated thermodynamic properties. The numbers at the top of the columns refer to FIG. 1.

TABLE 15

| Compound or variable | 540 Feed Mixture | 570 Column (510) distillate | 566 HF product | 585 Column (520) distillate | 586 HFC-43-10mee product |
|---|---|---|---|---|---|
| HF, mol % | 83.6 | 83.0 | 100 | 92.5 | 100 |
| HFC-43-10mee, mol % | 16.4 | 17.0 | — | 7.5 | — |
| Temp., °C. | — | 97.5 | 109 | 23.8 | 65.8 |
| Pres., psi (kPa) | — | 184.7 (1273) | 186.7 (1287) | 19.7 (136) | 21.7 (150) |

What is claimed is:

1. An azeotrope or near-azeotrope composition comprising Z-HFC-1429 and hydrogen fluoride.
2. The azeotrope or near-azeotrope composition of claim 1 comprising Z-HFC-1429 and an effective amount of hydrogen fluoride.
3. The azeotrope or near-azeotrope composition of claim 1 comprising from about 10.3 mole percent to about 35.2 mole percent Z-HFC-1429 and hydrogen fluoride.
4. The azeotrope or near-azeotrope composition of claim 1 comprising from about 10.3 mole percent to about 35.2 mole percent Z-HFC-1429 and from about 89.7 mole percent to about 64.8 mole percent hydrogen fluoride.

5. The azeotrope or near-azeotrope composition of claim 1 comprising from about 10.3 mole percent to about 35.2 mole percent Z-HFC-1429 and from about 89.7 mole percent to about 64.8 mole percent hydrogen fluoride, wherein the vapor pressure is from about 4.1 psi (28.3 kPa) to about 285 psi (1965 kPa) at a temperature of from about −20° C. to about 100° C.

6. The azeotrope or near-azeotrope composition of claim 1 wherein said composition consists essentially of from about 10.3 mole percent to about 35.2 mole percent Z-HFC-1429 and from about 89.7 mole percent to about 64.8 mole percent hydrogen fluoride, wherein the vapor pressure is from about 4.1 psi (28.3 kPa) to about 285 psi (1965 kPa) at a temperature of from about −20° C. to about 100° C.

7. The azeotrope composition of claim 1 comprising from about 11.4 mole percent to about 32.6 mole percent Z-HFC-1429 and from about 88.6 mole percent to about 67.4 mole percent hydrogen fluoride, wherein the vapor pressure is from about 4.1 psi (28.3 kPa) to about 285 psi (1965 kPa) at a temperature of from about −20° C. to about 100° C.

8. The azeotrope composition of claim 1 wherein said composition consists essentially of from about 11.4 mole percent to about 32.6 mole percent Z-HFC-1429 and from about 88.6 mole percent to about 67.4 mole percent hydrogen fluoride, wherein the vapor pressure is from about 4.1 psi (28 kPa) to about 285 psi (1965 kPa) at a temperature of from about −20° C. to about 100° C.

9. The azeotrope or near-azeotrope composition of claim 1, wherein said composition is characterized by a difference between dew point pressure and bubble point pressure that is less than or equal to 3%, based upon bubble point pressure.

* * * * *